(12) United States Patent
Sarder et al.

(10) Patent No.: US 10,862,414 B2
(45) Date of Patent: Dec. 8, 2020

(54) CARBON MONOXIDE SHUTOFF SYSTEM FOR ELECTRIC GENERATOR

(71) Applicant: Champion Power Equipment, Inc., Santa Fe Springs, CA (US)

(72) Inventors: Mark Sarder, Santa Fe Springs, CA (US); Mark Kastner, Santa Fe Springs, CA (US); Zhikun Zhong, Santa Fe Springs, CA (US); James Dehn, Santa Fe Springs, CA (US); Hiroaki Sato, Santa Fe Springs, CA (US)

(73) Assignee: Champion Power Equipment, Inc., Santa Fe Springs, CA (US)

( * ) Notice: Subject to any disclaimer, the term of this patent is extended or adjusted under 35 U.S.C. 154(b) by 0 days.

(21) Appl. No.: 16/122,337

(22) Filed: Sep. 5, 2018

(65) Prior Publication Data

US 2020/0036310 A1    Jan. 30, 2020

Related U.S. Application Data

(60) Provisional application No. 62/711,329, filed on Jul. 27, 2018.

(51) Int. Cl.
*G08B 17/10*  (2006.01)
*H02P 9/02*   (2006.01)
(Continued)

(52) U.S. Cl.
CPC .............. *H02P 9/02* (2013.01); *F02D 41/042* (2013.01); *G01N 33/004* (2013.01); *H02J 7/00* (2013.01); *H02J 7/345* (2013.01)

(58) Field of Classification Search
CPC .......... F16K 17/36; F17C 13/00; F17C 13/02; F17C 13/12; F17C 2205/0326; F17C 2221/035; F17C 2223/0153; F17C 2223/033; F17C 2225/0123; F17C 2250/032; F17C 2250/034; F17C 2250/0452; F17C 2250/0636; F17C 2260/044; F17C 2265/04; F17C 2270/0165; F17D 5/06; G01M 3/002; G01M 3/20; G01M 3/38; G01N 33/004; Y02A 50/243;
(Continued)

(56) References Cited

U.S. PATENT DOCUMENTS

| 6,025,788 A * | 2/2000 | Diduck ................... G01M 3/18 340/3.4 |
| 6,208,256 B1 | 3/2001 | Fleming et al. |

(Continued)

*Primary Examiner* — Daniel Previl
(74) *Attorney, Agent, or Firm* — Stetina Brunda Garred & Brucker

(57) ABSTRACT

A carbon monoxide shutoff system for an engine of a portable electrical generator has a carbon monoxide gas sensor, a microcontroller, and an output indicator. The carbon monoxide gas sensor generates an output electrical current proportional to a detected concentration of ambient carbon monoxide. The microcontroller has an input connected to the carbon monoxide gas sensor, and an output connected to an operational control of the engine. A deactivation signal generated by the microcontroller in response to detection of a deactivation condition is based upon the output electrical current from the carbon monoxide gas sensor matching predefined value and duration thresholds. The deactivation signal is operative to stop the engine.

11 Claims, 4 Drawing Sheets

(51) Int. Cl.
 *F02D 41/04* (2006.01)
 *G01N 33/00* (2006.01)
 *H02J 7/00* (2006.01)
 *H02J 7/34* (2006.01)

(58) Field of Classification Search
 CPC ......... Y10T 137/1915; Y10T 137/1939; Y10T 436/12; Y10T 436/205831
 USPC ..... 340/632, 3.4, 3.1, 3.9, 604–605, 825.69, 340/825.72, 506
 See application file for complete search history.

(56) References Cited

U.S. PATENT DOCUMENTS

| | | | |
|---|---|---|---|
| 6,433,696 B1 | 8/2002 | Deiterman et al. | |
| 6,503,141 B2 | 1/2003 | Meneely | |
| 6,552,647 B1* | 4/2003 | Thiessen | G05B 15/02 122/448.1 |
| 6,743,091 B2 | 6/2004 | Meneely | |
| 6,989,757 B2 | 1/2006 | Geoffrey et al. | |
| 7,183,933 B2 | 2/2007 | Dzurko et al. | |
| 7,710,284 B2 | 5/2010 | Dzurko et al. | |
| 8,054,188 B2 | 11/2011 | Harkins et al. | |
| 8,286,603 B2 | 10/2012 | Sid | |
| 8,791,828 B2 | 7/2014 | Harkins et al. | |
| 9,053,626 B2 | 6/2015 | Cristoforo | |
| 9,058,739 B2 | 6/2015 | Sid | |
| 10,184,374 B2* | 1/2019 | Han | F01N 3/2825 |
| 2002/0111132 A1 | 8/2002 | Meneely, Jr. | |
| 2003/0020619 A1* | 1/2003 | Winters | A62B 9/006 340/632 |
| 2003/0087600 A1 | 5/2003 | Meneely, Jr. | |
| 2004/0160329 A1* | 8/2004 | Flanc | G08B 17/10 340/632 |
| 2005/0212681 A1 | 9/2005 | Dzurko et al. | |
| 2007/0085692 A1 | 4/2007 | Grant et al. | |
| 2007/0182574 A1 | 8/2007 | Dzurko et al. | |
| 2008/0182215 A1 | 7/2008 | Sid | |
| 2010/0171608 A1 | 7/2010 | Harkins et al. | |
| 2012/0055235 A1 | 3/2012 | Harkins et al. | |
| 2012/0310547 A1* | 12/2012 | Cristoforo | G08B 21/14 702/24 |
| 2013/0021119 A1 | 1/2013 | Sid | |
| 2013/0021160 A1 | 1/2013 | Sid | |
| 2015/0057912 A1 | 2/2015 | Ortmann et al. | |
| 2015/0268210 A1 | 9/2015 | Cristoforo | |
| 2015/0276693 A1 | 10/2015 | Sid | |
| 2019/0226595 A1* | 7/2019 | Mattos | F17C 13/12 |

\* cited by examiner

CARBON MONOXIDE SHUTOFF SYSTEM FOR ELECTRIC GENERATOR

CROSS-REFERENCE TO RELATED APPLICATIONS

The application relates to and claims the benefit under 35 U.S.C. § 119(e) to U.S. Provisional Patent Application No. 62/711,329 filed Jul. 27, 2018 and entitled "CARBON MONOXIDE SHUTOFF SYSTEM FOR ELECTRIC GENERATOR" the entire contents of which is wholly incorporated by reference herein.

STATEMENT RE: FEDERALLY SPONSORED RESEARCH/DEVELOPMENT

Not Applicable

BACKGROUND

1. Technical Field

The present disclosure relates generally to electric generators and safety devices therefor, and more particularly, to a carbon monoxide shutoff system for electric generators.

2. Related Art

Electrical generators are used to convert mechanical energy into electrical energy. There are innumerable configurations and sizes of electrical generators that find application in various contexts. These include powering national, regional, and local electrical grids, providing backup or secondary power to a specific location or building in case of a fault in the electrical grid, as well as serving as a primary power source at locations where transmission lines from an electric utility have not yet been extended, or where there is only a temporary need for electrical power.

Depending on the application, a generator may use different mechanical sources and are therefore configured with particular devices that generate and/or harness mechanical energy, such as steam, gas, or water turbines, or internal combustion engines. The mechanical energy as it is output from these devices is typically a rotational motion or a linear reciprocal motion, and is converted to electrical energy with dynamos (for DC power) or alternators (for AC power).

Specifically, dynamos or alternators include an armature, which is a coil or a series of conductive windings that are placed in proximity to a magnet. The armature is mechanically moved about the magnet, thereby generating an electromotive force that drives an armature electrical current. This electrical current is relayed to the various electric devices connected to the generator.

A portable generator is useful where power generation requirements are at the individual or group level, as electrical power can be immediately available in locations that are otherwise lacking in service from a central utility. For example, new construction sites require electricity to power tools utilized in the construction activity, but it is not always the case that the electrical utility has constructed power lines thereto. Portable generators may be brought to the construction site to provide the needed electricity. In another example, portable generators may be used to provide electrical power to run household appliances such as refrigerators, microwave ovens, as well as lighting while camping in remote wilderness locations that have no power connections. Portable generators are also frequently purchased for home use to provide backup power during an emergency where electrical power from the central utility is intermittent or unavailable altogether.

In a typical configuration, the portable generator incorporates the aforementioned mechanical energy source and the electromagnetic generators, e.g., the dynamo or the alternator, in a single standalone unit. The mechanical energy source, as noted above, may be an internal combustion engine that is powered by fuel such as gasoline, diesel, propane, and natural gas. The storage for such fuel is also incorporated into the portable generator, along with various fuel delivery and engine control components. The engine may also be equipped with exhaust systems that limit noise and emissions, as well as cooling and internal lubrication systems.

The frequency and shape of an alternating current signal output by the generator may vary depending on the operation of the engine, so a governor that regulates its speed may be utilized. Alternatively, the directly generated alternating current signal may be filtered and rectified into a direct current (DC) voltage, and converted back to a consistently shaped and timed alternating current (AC) signal with a power inverter. The operational details of the portable generator is typically reported by onboard indicators such as voltmeters, ammeters, fuel low indicators, oil low indicators, generated frequency, and timers/counters.

Portable generators, like all fuel-burning appliances, generate exhaust gasses. Although specific composition ratios vary, exhaust gasses from the combustion of fuel and air in gasoline, diesel, and other internal combustion engines include nitrogen, carbon dioxide, oxygen, nitrogen oxides, carbon monoxide, hydrocarbons, and sulfur dioxide, as well as other harmful particulate matter. One of the most harmful exhaust gasses is carbon monoxide, which is an invisible, odorless, colorless, and non-irritant gas that is generated from the incomplete combustion of fuel that prevents complete oxidation to carbon dioxide.

An exposure to high concentrations of carbon monoxide can result in the loss of consciousness, seizures, arrhythmias, and even death. Short of death or loss of consciousness, those with acute carbon monoxide poisoning from exposure to lower concentrations of carbon monoxide may experience a variety of symptoms such as headaches, dizziness, weakness, chest pains, and the like. It is understood that carbon monoxide combines with the hemoglobin of the blood to form carboxyhemoglobin, which prevents it from carrying oxygen throughout the circulation system of the body.

The operation of portable generators within enclosed or semi-enclosed spaces is one of the most common causes for carbon monoxide poisoning. During wintertime in locales where snowfall occurs, the consequent power outages necessitate the use of portable generators. Although numerous warnings not to operate portable generators within the home, garage, or other enclosed space with adequate ventilation accompany the products, environmental conditions may not be conducive to safer operation. For example, ongoing rain or snow, or accumulated snow may make it difficult to run the portable generator outside the enclosed spaces of the home or garage.

Portable generators are not the only source of carbon monoxide emissions in a typical household, as cooking equipment, heating appliances such as furnaces, space heaters, and fireplaces, as well as motor vehicles all output carbon monoxide. Various approaches have been taken to minimize the possibility of carbon monoxide poisoning, one of the most prevalent being carbon monoxide alarms installed throughout an interior space. A wide range of sensing technologies are known in the art, including optochemical detectors that generate an alarm based upon the color of a chemical pad changing in response to carbon monoxide exposure, electrochemical sensors that generate an alarm based upon an electrical signal that relates to concentration levels of carbon monoxide, as well as semiconductor sensors that generate an alarm based upon electrical circuit parameters (e.g., resistance) that changes with exposure to carbon monoxide. Beyond visual and audible alarms that are activated when unsafe levels of carbon monoxide are detected within an atmosphere, affirmative actions may be initiated, such as the activation of air circulation fans, opening doors/windows within the enclosed space, shutting down the equipment generating the carbon monoxide, and so forth.

Although there are several known systems for stopping the operation of a portable generator where high concentrations of carbon monoxide are present at the engine exhaust and areas proximate thereto, there continues to be a need for improved shutoff devices.

BRIEF SUMMARY

The present disclosure is directed to a carbon monoxide sensing module that shuts down a portable generator when a carbon monoxide concentration above certain preset levels is detected.

One embodiment is a carbon monoxide shutoff system for an engine of a portable electrical generator that is generally comprised of a carbon monoxide gas sensor, a microcontroller, and an output indicator. The carbon monoxide gas sensor may generate an output electrical current proportional to a detected concentration of ambient carbon monoxide. The microcontroller may have an input that is connected to the carbon monoxide gas sensor, and an output that is connected to an operational control of the engine. A deactivation signal generated by the microcontroller from the output thereof in response to detection of a deactivation condition may be based upon the output electrical current from the carbon monoxide gas sensor matching predefined value and duration thresholds. The deactivation signal may be operative to stop the engine. The output indicator may be connected to the microcontroller. A deactivation notification sequence may be generated on the output indicator in response to the detection of the deactivation condition.

Another embodiment of the present disclosure is a portable electrical generator. There may be an internal combustion engine that includes an electrical ignition system with an ignition coil. There may also be an engine deactivator that is connected to the electrical ignition system of the internal combustion engine. The engine deactivator may include a carbon monoxide gas sensor generating an output electrical current proportional to a detected concentration of ambient carbon monoxide. The engine deactivator may also include a microcontroller with an input connected to the carbon monoxide gas sensor, and an output connected to the ignition coil. A deactivation signal may be generated by the microcontroller from the output thereof in response to detection of a deactivation condition, which in turn may be based upon the output electrical current from the carbon monoxide gas sensor matching predefined value and duration thresholds. The deactivation signal may be operative to restrict an ignition electrical signal to the ignition coil.

Yet another embodiment of this disclosure is a method for deactivating an engine of a portable electrical generator. The method may include a step of receiving an output electrical current proportional to a detected concentration of ambient carbon monoxide from a carbon monoxide gas sensor. There may also be a step of deriving an ambient carbon monoxide concentration value from the received output electrical current. Thereafter, the method may include evaluating, on a controller, within a first control loop while the ambient carbon monoxide concentration value is below a lower threshold, a voltage value from a power supply circuit to the controller. This first control loop may be maintained while the voltage value corresponds to electrical continuity with the controller, as well as an active status corresponding to a regular ongoing reception of the output electrical current. The method may also include initiating a pre-shutoff loop on the controller. This may be in response to the ambient carbon monoxide concentration being above an upper threshold. The pre-shutoff loop may include evaluating a plurality of carbon monoxide concentration values over a predetermined duration. There may also be a step of generating an engine deactivation signal from the controller in response to the plurality of carbon monoxide concentration values of the predetermined duration meeting an acceptance criterion. The foregoing method may be implemented as a series of instructions executable by a data processor and tangibly embodied in a program storage medium.

The present invention will be best understood by reference to the following detailed description when read in conjunction with the accompanying drawings.

BRIEF DESCRIPTION OF THE DRAWINGS

These and other advantages and features of the invention will be better appreciated in view of the following drawings and descriptions in which like numbers refer to like parts throughout, and in which.

DETAILED DESCRIPTION

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure. It is further understood that the use of relational terms such as first and second and the like are used solely to distinguish one entity from another without necessarily requiring or implying any actual such relationship or order between such entities.

Figure 1:
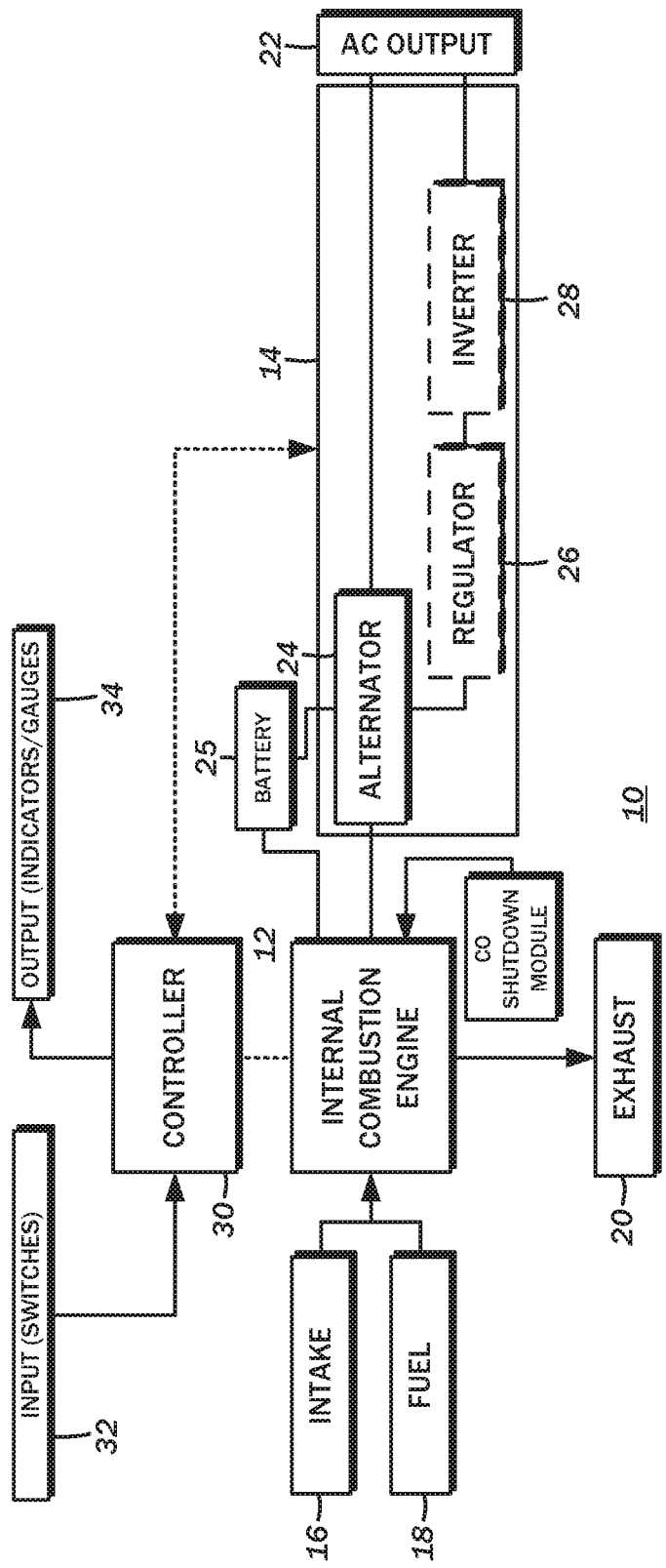
FIG. 1 is a block diagram showing an exemplary portable generator including a carbon monoxide shutoff module in accordance with one embodiment of the present disclosure.

Referring to the block diagram of FIG. 1, one contemplated embodiment of the present disclosure is an electrical generator unit 10 with deactivation features that are, in general, triggered in response to certain environmental conditions. The present disclosure makes reference to a "portable" electrical generator unit 10, that is, a generator that is not permanently installed, and can be moved from one location to another as the need for electrical power arises. However, this is by way of example only and not of limitation, and it is to be understood that embodiments of the present disclosure can be utilized in other contexts and different types and configurations of electrical generators.

As is typical for most conventional implementations, the electrical generator unit 10 includes an internal combustion engine 12 that outputs mechanical energy that is then converted to electrical energy with an electromagnetic generator 14. The engine 12 has an air intake 16 and a fuel source 18, the combination of which is mixed and ignited within a cylinder to move a reciprocating piston. The combusted gasses are also output from an exhaust 20. The piston, in turn, is understood to be mechanically connected to a rotor of the electromagnetic generator 14. According to various embodiments, the engine 12 may be a four-stroke engine or a two-stroke engine that uses gasoline as its fuel, a diesel engine, or any other suitable engine. Further, simpler engine control configurations using carburetors to meter the fuel and distributors to time the ignition of the fuel may be utilized, as well as more modern fuel injected and computer-controlled ignition. The size/displacement of the engine 12 may be varied according to the power ratings of the electrical generator unit 10. The principles of operation and the numerous available configurations of the engine 12 are well known in the art, so a detailed consideration of each possible variation that may find use in the electrical generator unit 10 will be omitted.

Either the rotor or the stator includes a magnet, while the other includes an armature comprised of wire windings. The generated magnetic flux is understood to induce a corresponding electrical current in the armature, which is in electrical communication with an electrical output 22. The electromagnetic generator 14 may be an alternator 24 that outputs an alternating current (AC) power to the electrical output 22. The electrical power needed to start and continue to operate the engine 12 may be provided by a battery 25 that is charged from the alternator 24.

Some implementations of the electrical generator unit 10 output the AC signal directly from the alternator 24. Because the generated current must be the same as that which is generated by the power grid, e.g., 120V at 60 Hz, or any other standard, there may be additional control modalities to drive the engine 12 at varying speeds to drive the alternator 24 to maintain constant output. In this regard, different environmental conditions that alters the output speed of the engine driveshaft, that is, the rotor of the alternator, may impact the AC current available from the electrical output 22.

An alternative configuration known as the inverter generator may utilize the potentially erratic AC power from the alternator 24, and rectifies and filters that current in a regulator circuit 26 to generate a steady direct current DC output. The DC current is then utilized to drive an inverter circuit 28 that programmatically generates a precisely timed and clean sinusoidal AC current that does not change in response to differing mechanical output from the engine 12. The output from the inverter circuit 28 is likewise passed to the electrical output 22.

The higher level control functions for the engine 12 and the electromagnetic generator 14 may be handled by a controller 30, which is understood to be a microcontroller or integrated data processing device with input and output capabilities. The microcontroller may be programmed with instructions that accept inputs and generates outputs in response to the inputs, and perform various steps in accordance with embodiments of the present disclosure. In this regard, the microcontroller may include memory modules (both read/write capable and read-only varieties). At a basic level, the controller 30 accepts commands from one or more input devices 32, which may be a simple toggle or push-button switch that powers on the electrical generator unit 10, an engine starter button, and the like. Additionally, some embodiments also contemplate the use of remote control devices that may communicate over wired signal transmission lines, or wirelessly via radio frequency (RF), infrared, and the like. All such devices are understood to be encompassed within the illustrated feature of the input devices 32. Still further, smartphones, tablets, and other general purpose communications devices may generate commands that are received by the controller 30, and thus may likewise be considered input devices 32.

The controller 30 may also generate information that is presented on one or more output devices 34. These may include indicators that show the operational parameters of the electrical generator unit 10, including voltmeters (to show the output voltage at the electrical output 22), ammeters (to show instantaneous current output at the electrical output 22), fuel low indicators, oil low indicators, power output current frequency, and operating timers/counters. The indicators may be as simple as on/off lights that are activated when a fault condition is detected. The aforementioned remote control devices may also include indicators, as well as smartphones and tablets that may present historical values alongside the current/instantaneous values.

Various embodiments of the electrical generator unit 10 contemplate the automatic shutoff of the engine 12 when there has been an accumulation of harmful gasses, including carbon monoxide. As was discussed above, carbon monoxide is odorless, colorless, and non-irritating, but exposure to even moderate concentrations can be harmful. Operating the electrical generator unit 10 in enclosed spaces has the potential to increase the concentration of carbon monoxide to dangerous levels, so the cessation of the internal combustion engine generating this poisonous gas is contemplated in accordance with the present disclosure. To this end, the electrical generator unit 10 includes a carbon monoxide shutoff module 36. Reference to the shutoff module being related to carbon monoxide, however, is by way of example only, and not of limitation. The embodiments of the present disclosure may be adapted for shutting down the electrical generator unit 10 based on concentration levels of other harmful gasses, in which case, the module may be referred to with such other gasses. Thus, on a more general level, the carbon monoxide shutoff module 36 may also be referenced as an engine deactivator.

Figure 2:
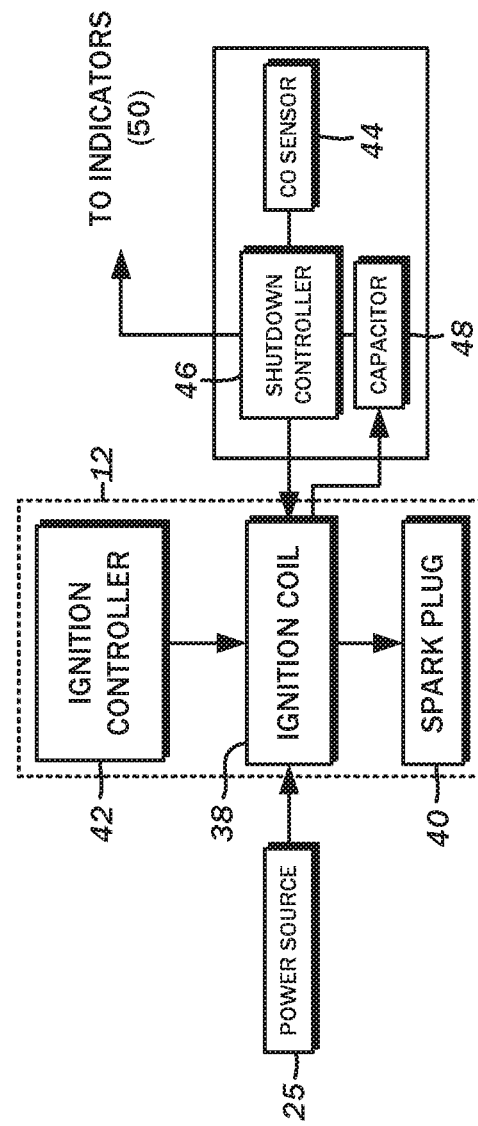
FIG. 2 is a block diagram of one embodiment showing additional details of the carbon monoxide shutoff module.

As shown in both block diagrams of FIG. 1 and FIG. 2, the carbon monoxide shutoff module 36 is connected to the engine 12, and in one embodiment, an ignition coil 38 thereof. It is understood that the air-fuel mixture within the cylinder of the engine 12 is ignited by a spark plug 40. The relatively low voltage from the battery 25 is increased by the ignition coil 38 so that a spark may be generated by the spark plug 40. The signal to activate the spark plug 40 may originate from an ignition controller 42, which may be electrically isolated from the high voltage output of the ignition coil 38. Although specific reference has been made to a battery-powered ignition system, this may be replaced with a magneto ignition system that is activated by the rotation of the engine.

The carbon monoxide shutoff module 36 may include a carbon monoxide gas sensor 44 that generates an output electrical current that is proportional to a detected concentration of ambient carbon monoxide. In one embodiment, the carbon monoxide gas sensor 44 is an electrochemical sensor comprised of electrodes that oxidizes the carbon monoxide present, with the remaining hydrogen ions migrating into an acidic aqueous electrolyte. The electrons generated at the electrode, when connected to an external source, form a small current at the nano-ampere (nA) level. A sensor of this configuration may be the NAP-508 available from Nemoto Sensor Engineering Company Ltd. of Tokyo Japan, though any other suitable carbon monoxide sensor of alternative types such as semiconductor-type and biomimetic type sensors may be substituted without departing from the present disclosure. An electro-chemical sensor is understood to be advantageous because of its linear response, fast response and recovery time, high selectivity, humidity independence, mechanical durability, and requiring no external power.

The carbon monoxide shutoff module 36 includes a microcontroller 46 with an input port that is connected to the carbon monoxide gas sensor 44, and an output that is connected to the ignition coil 38. The input port of the microcontroller 46 may be a single line that is configured to receive an electrical current, with internal circuitry that measures the analog current and converts the same to an equivalent digital value. The microcontroller may be an Atmel ATtiny861A microcontroller from Microchip Technology, Inc. of Chandler, Ariz., though any other suitable integrated microcontroller device that has sufficient performance, power consumption, and input/output capabilities to implement the various embodiments of the present disclosure may be used. The exemplary implementation utilizes a processor clock frequency of 128 kHz, though it need not be restricted thereto. One or more of the components of the carbon monoxide shutoff module 36, e.g., the carbon monoxide gas sensor 44 and the microcontroller 46, may be embedded or otherwise disposed within an enclosure of the ignition coil 38.

The specific gain response of each carbon monoxide gas sensor 44 may vary due to manufacturing differences, so the present disclosure contemplates an initial calibration routine at each startup. During the manufacturing process, an electrically erasable programmable read-only memory (EEPROM) connected to the microcontroller 46 may be programmed with a gain value of the carbon monoxide gas sensor 44 that is being utilized. By way of example, if the carbon monoxide sensor generates 2.865 nA/ppm (parts per million) of carbon monoxide, a value of "2865" may be indicated. This indication may be encoded as a bar code, or printed on material that is associated with the particular sensor. When read, the EEPROM can be programmed with the number "2865," which corresponds to the hexadecimal number B31. A specific memory location in the EPPROM is programmed with B31, and during the calibration process, the microcontroller 46 may read the same memory location to modify the gain factor to determine the corresponding carbon monoxide concentration levels. In an alternative embodiment, the microcontroller 46 may regularly read the EEPROM location for this data. This embodiment is not understood to require a calibration procedure, and the data in the particular memory location is retrieved whenever needed.

In response to the detected carbon monoxide concentration levels, the microcontroller 46 may generate a deactivation signal to the ignition coil 38. More specifically, a deactivation condition may be detected based upon the output electrical current from the carbon monoxide gas sensor 44 matching predefined value and duration thresholds. The deactivation signal, in turn, may be operative to stop the engine 12 by restricting the ignition electrical signal to the ignition coil 38. In this context, the ignition coil 38 may be referred to as the operational control. Alternative operational controls that governs the operation of the engine 12 may be substituted in accordance with different embodiments of the present disclosure. Further integration with the electronic fuel injection (EFI) system and the various components thereof is contemplated, including the fuel injector, the fuel pump, the stepper motor for fuel and air delivery, in addition to the aforementioned ignition coil. Furthermore, carbureted engines may also be utilized, in which case the operational control may be a fuel cut solenoid, which may be mounted on the bottom of a float feed carburetor. Various configurations contemplate either a normally open or a normally closed setting, such the operational control signal to the fuel cut solenoid is operative to remove power and close the solenoid without power, or to continuously actuate the solenoid to keep it closed. When the solenoid is closed and fuel supply is stopped, the carburetor may be cut off, thereby shutting down the engine within a few seconds. The specific value and duration thresholds, and the manner in which this data is processed, e.g., the deactivation condition, will be described in further detail below.

Whenever taking action with respect to the engine 12, the microcontroller 46 also generates information to one or more output indicators 50. According to various embodiments of the present disclosure, the output indicator 50 is connected to the microcontroller 46, and may be remote from the carbon monoxide gas sensor 44, as well as the microcontroller 46. However, the output indicator 50 is nevertheless deemed to be part of the carbon monoxide shutoff module 36. One embodiment contemplates the use of multi-colored light emitting diodes LEDs as the output indicator 50, though this is by way of example only and not of limitation. Contemporaneously with the shutoff of the engine 12, the microcontroller 46 generates a deactivation notification sequence on the output indicator 50. Thus, the deactivation notification sequence is in response to the detection of the aforementioned deactivation condition.

As discussed above, the carbon monoxide gas sensor 44 is self-powering, and the microcontroller 46 is powered by an electrical current tapped from the ignition coil 38. More particularly, the carbon monoxide shutoff module 36 includes a power supply capacitor 48 that supplies power to the microcontroller 46 after the engine 12 has been shut off, and there is no longer power from the ignition coil 38. In this regard, a battery that would otherwise be required to power the microcontroller 46 can be eliminated. Along the same lines, a battery that may be needed to power the output indicator 50 may also be eliminated, and powered for a limited time from the power supply capacitor 48.

Some embodiments of the electrical generator unit 10 include a remote starter, which may be a combined input device 32 and output device 34 in the context of the block diagram of FIG. 1. Under some circumstances, the user may restart the electrical generator unit 10 after a shutoff event, provided that the unsafe condition that necessitated it in the first place passes. The remote starter may be in communication with either the controller 30 of the electrical generator unit 10, or specifically the microcontroller 46 of the carbon monoxide shutoff module 36. The remote starter is understood to generate a remote restart command in response to a user input, and may be conditionally operative to restart the engine 12 because the carbon monoxide concentration levels is checked to confirm safe levels before restarting.

Under other conditions that are deemed to be unsafe, the restart may be disabled. Further details on the methodology of allowing or disallowing restarts will be considered below.

Figure 3:
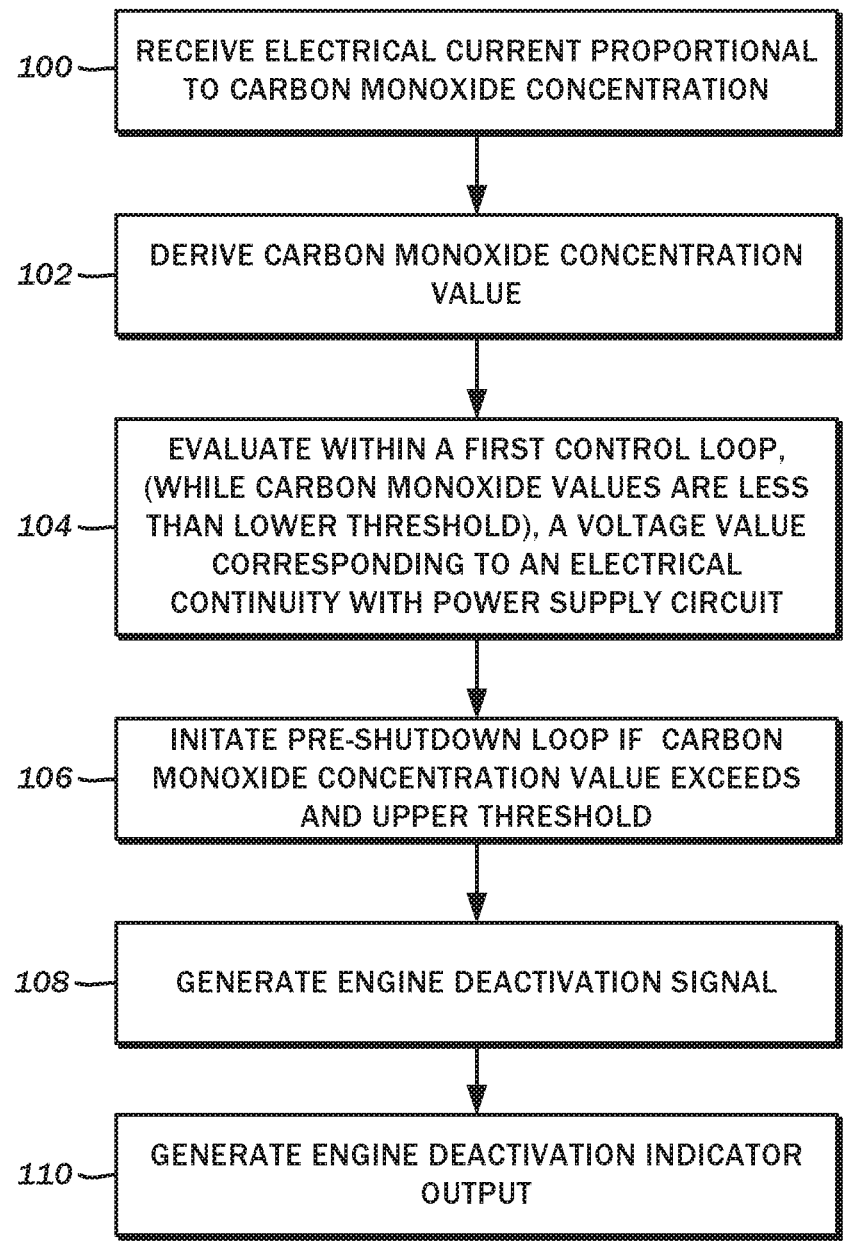
FIG. 3 is a flowchart depicting an embodiment of a method for deactivating an engine of the portable generator.

The present disclosure contemplates various embodiments of methods for deactivating the engine 12 of the electrical generator unit 10. With reference to the flowchart of FIG. 3, one method begins with a step 100 of receiving the output electrical current of the carbon monoxide gas sensor 44. As discussed above, this electrical current is proportional to the detected concentration of ambient carbon monoxide. Then, also as considered previously, there is a step 102 of deriving an ambient carbon monoxide concentration value from the output electrical current. With the carbon monoxide gas sensor 44 generating increasing levels of current in response to carbon monoxide concentration levels, the measured current can be computed to a specific concentration value.

The aforementioned steps 100 and 102 of receiving the output of the carbon monoxide gas sensor 44 and deriving the carbon monoxide concentration level continues throughout. In a first control loop per illustrated step 104, the microcontroller 46 may evaluate the carbon monoxide concentration value, and so long as it is below a lower threshold, further evaluate a voltage value from a power supply circuit to the microcontroller 46. The power supply circuit in one embodiment is understood to be the connection between the power supply capacitor 48 and the ignition coil 38, as well as components connected thereto that serve a power supply function. So long as the voltage value is that which corresponds to an active status in which there is a regular ongoing reception of the output electrical current, e.g., the carbon monoxide shutoff module 36 has not been disconnected for any reason, and the other aforementioned conditions are maintained, the first control loop continues. However, it is also possible to power the carbon monoxide shutoff module 36 with a battery that is utilized as part of the engine ignition system, or the additional winding in a magneto-based implementation.

According to next step 106, the microcontroller 46 initiates a pre-shutoff loop if or once the carbon monoxide concentration value exceeds an upper threshold. The pre-shutoff loop involves an evaluation of a plurality of carbon monoxide concentration values over a predetermined duration. The loop exiting conditions or acceptance criterion may be, for example, if the average of the carbon monoxide concentration value over a certain timespan exceeds a limit. Once this pre-shutoff loop is exited, execution continues to a step 108 of generating the engine deactivation signal. Stated alternatively, the step 108 takes place when a plurality of carbon monoxide concentration values of the predetermined duration meet an acceptance criterion.

There may also be a substantially contemporaneous step 110 of generating an engine deactivation indicator output on the output indicator 50, or other remove visual indication device. As utilized herein, substantially contemporaneous is understood to mean around the same time. The microcontroller 46 may execute the instructions generating the engine deactivation signal before or after generating the corresponding output, but from the perception of the user viewing the electrical generator unit 10 and the output indicator 50, it may appear to occur simultaneously. There may also be a delay between the engine 12 deactivating and the output indicator 50 illuminating. However, so long as the user has the perception that the indicator in general accurately reflects the current status of the electrical generator unit 10, it is to be considered substantially contemporaneous.

Figure 4:
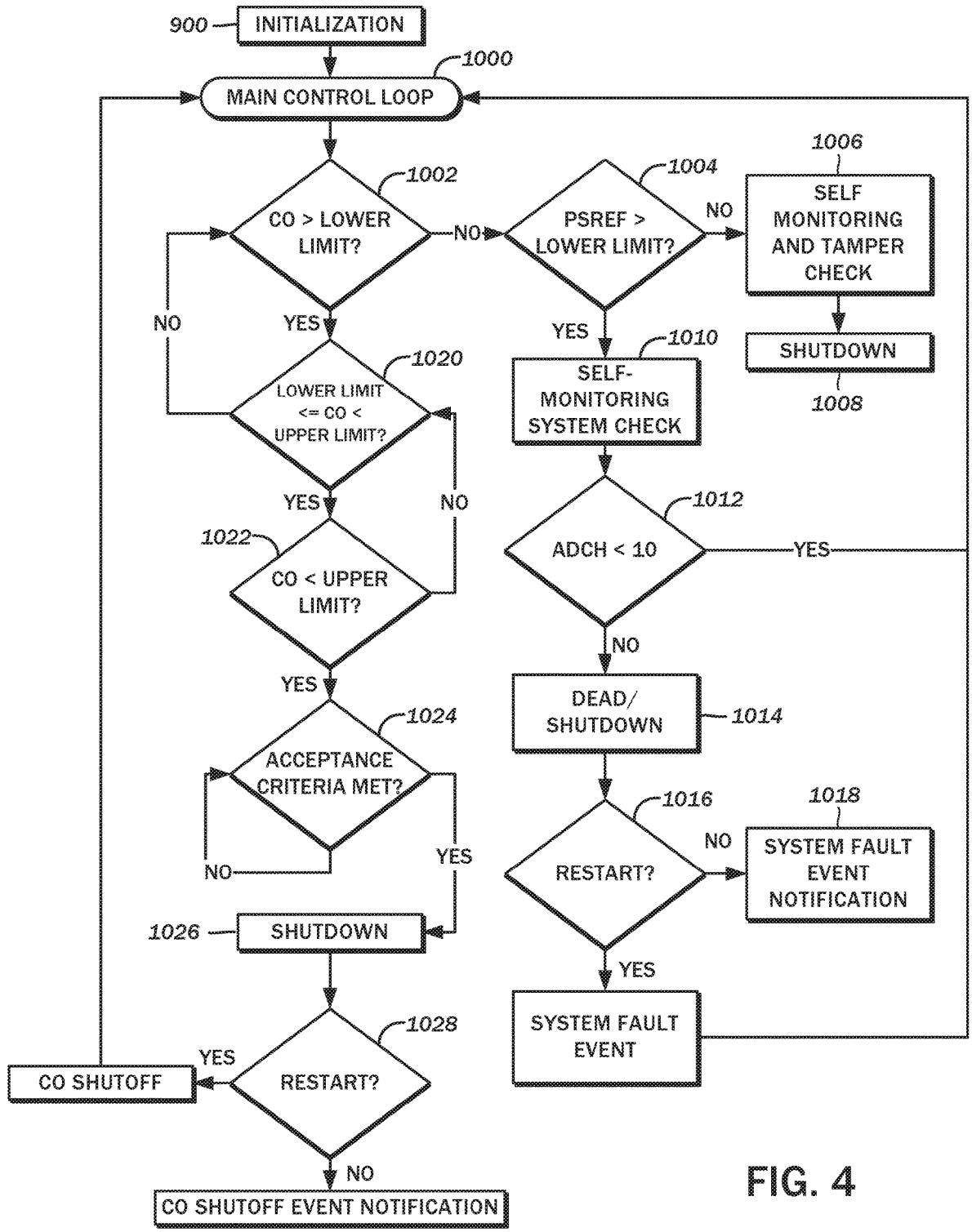
FIG. 4 is a flowchart showing additional details of the control loops implemented by the carbon monoxide shutoff module.

Additional details of the process and methodology implemented by the carbon monoxide shutoff module 36 will now be considered with reference to the flowchart of FIG. 4. Prior to beginning a main control loop 1000, there is an initialization step 900 in which the aforementioned EEPROM values are read to retrieve the sensor gain value. A short time delay of, for example, four seconds, is also introduced to stabilize the carbon monoxide gas sensor 44. Optionally, though preferably, a watchdog timer is also set to allow for a graceful exit in case of a stuck loop. Additionally, the presence of a remote and/or local output indicator 50 is determined, with all subsequent indicator outputs being directed to the one that is available.

Upon entering the main control loop 1000, there are a series of evaluations of the derived carbon monoxide concentration value, as well as other signals and voltages that were generally described above. In a first decision branch 1002, the carbon monoxide concentration value is determined whether it is greater than a first lower concentration limit. If not, the process enters a second decision branch 1004 to evaluate whether the power supply reference voltage is greater than 0.75V. This evaluation may be made once every minute. In one embodiment the power supply reference voltage as determined by the microcontroller 46, PSREF, is given as an integer, so the evaluation is whether this is less than or greater than a second lower concentration limit value. If less than the second lower concentration limit value, it is assumed in a step 1006 that the power supply wire to the carbon monoxide shutoff module 36 was cut or tampered with, and the system proceeds to shut off the electrical generator unit 10 in accordance with a step 1008. There is contemplated to be no restrictions as to how quickly this takes place. Additionally, no outputs are generated to the output indicators 50, and no data is saved to memory.

If, on the other hand, the PSREF is greater than the second lower concentration limit value 75, then a self-monitoring system determines whether the carbon monoxide shutoff module 36 is live or dead in a step 1010. More particularly, the port of the microcontroller 46 to which the carbon monoxide gas sensor 44 is connected is driven high for an initial state, then pulsed logic low for an exemplary 70 milliseconds. With the analog-to-digital converter of the microcontroller 46 thereafter deriving the voltage on the sensor input port, the carbon monoxide level value (COLEV) is understood to change from 1 volt to the high level, and the ADCH (analog-to-digital converter high port) rises to may rise as high as 50. If the ADCH value is greater than 10 per a third decision branch 1012, the test is passed, and the process returns to the main control loop 1000. However, if lower than 10, the carbon monoxide gas sensor 44 is assumed to be dead per step 1014, and begins the shutoff procedure.

As mentioned above, different colors of output indicators 50 may be utilized. In an exemplary embodiment, a yellow color LED may be used to indicate a system fault event. Such yellow LED may be activated for twenty seconds, whether it be a remote or local output indicator 50. Thereafter, the LED may be blinked for 400 milliseconds on, and 1600 milliseconds off. A sensor failure event is recorded in memory, and the electrical generator unit 10 will be locked out for twenty seconds. These values are presented by way of example only and not of limitation, and may depend on the size of the power supply capacitor 48. A larger capacitance and charge-holding capability may lengthen the time in which the output indicator 50 can be illuminated, while a smaller capacitance may reduce the time.

Remotely restarting the electrical generator unit 10 may be allowed or disallowed as desirable. So long as no restart command is received as evaluated in a fourth decision branch 1016, the system keeps the yellow LED blinking for at least 5 minutes per step 1018. The blinking is understood to stop when the power supply capacitor 48 has no more energy. If a restart command is received as evaluated in the fourth decision branch 1016, the process returns to the main control loop 1000.

Returning to the first decision branch 1002, if the carbon monoxide concentration value is determined to be greater than a first lower concentration limit value, a fifth decision branch 1020 evaluates whether the carbon monoxide concentration value is between a first lower concentration limit and an upper concentration limit. During this time, the aforementioned live or dead check may be suspended. If between the first lower concentration limit and the upper concentration limit, the carbon monoxide concentration value continues to be evaluated, again in the first decision branch 1002. Otherwise, the carbon monoxide concentration value is evaluated whether it is greater than the upper concentration limit in a sixth decision branch 1022. If no, the carbon monoxide concentration value is evaluated in the fifth decision branch 1020, whether it is between the first lower concentration limit and the upper concentration limit.

When the carbon monoxide concentration value is greater than the upper concentration limit, the process continues to a seventh decision branch 1024 to determine whether certain acceptance criteria are met. This is understood to correspond to the aforementioned pre-shutoff loop 106, where a rolling average carbon monoxide concentration value for a set duration is evaluated. For example, one acceptance criteria is a second upper concentration limit of carbon monoxide concentration that is detected at least two consecutive readings. Another acceptance criteria is a rolling average of an upper concentration limit of carbon monoxide concentration readings over 5 minutes. In either case, the electrical generator unit 10 is shut off in accordance with step 1026, and the output indicator 50 is illuminated. The specific values of the concentration limits to select for the foregoing procedure may be varied, and are within the purview of those having ordinary skill in the art.

Due to the greater severity of the cause of this shut off, a red LED is envisioned. Two of the red LEDs may be turned solidly on for twenty seconds, then blinked for 400 milliseconds on, and 1600 milliseconds off. Again, the electrical generator unit 10 is locked out for twenty seconds, and the particular event that led to the shutoff is recorded in memory. Remote restart is also disabled, and the electrical generator unit 10 can only be restarted locally. If a local restart command is received as evaluated in an eighth decision branch 1028, the process returns to the main control loop 1000 following the shutoff event notification in a step 1030.

As the microcontroller 46 executes the instructions corresponding to the foregoing procedure, various data is recorded and stored. Additional diagnostic information such as the number of shutdowns, the type of each of those shutdowns, the total run-time, and the like may be stored in the EEPROM. These values may be retrieved by an externally connected diagnostic tool and/or viewed on a general-purpose computer system configured for reading and presenting such data. The specifics of logging diagnostic data is deemed to be within the purview of one having ordinary skill in the art, so no additional details thereof will be considered herein. The particulars shown herein are by way of example and for purposes of illustrative discussion of the embodiments of the present disclosure only and are presented in the cause of providing what is believed to be the most useful and readily understood description of the principles and conceptual aspects. In this regard, no attempt is made to show details of the present invention with more particularity than is necessary, the description taken with the drawings making apparent to those skilled in the art how the several forms of the present invention may be embodied in practice.

What is claimed is:

1. A portable electrical generator, comprising:
an internal combustion engine including electrical ignition system with an ignition coil;
an engine deactivator connected to the electrical ignition system of the internal combustion engine, the engine deactivator including:
a carbon monoxide gas sensor generating an output electrical current proportional to a detected concentration of ambient carbon monoxide; and
a microcontroller with an input connected to the carbon monoxide gas sensor, and an output connected to the ignition coil, a deactivation signal generated by the microcontroller from the output thereof in response to detection of a deactivation condition based upon the output electrical current from the carbon monoxide gas sensor matching predefined value and duration thresholds, the deactivation signal being operative to restrict an ignition electrical signal to the ignition coil.

2. The portable electrical generator of claim 1, further comprising an output indicator connected to the microcontroller and remote from the engine deactivator, a deactivation notification sequence being generated on the output indicator in response to the detection of the deactivation condition.

3. The portable electrical generator of claim 2, wherein the output indicator is one or more light emitting diodes.

4. The portable electrical generator of claim 1, wherein electrical power to the microcontroller and the output indicator is generated by the engine solely during active operation thereof.

5. The portable electrical generator of claim 4, further comprising a power supply capacitor connected to the power supply coil, the power supply capacitor being charged by the power supply electrical signal.

6. The portable electrical generator of claim 5, wherein the power supply capacitor provides the electrical power to the engine deactivator after the engine is deactivated and the ignition electrical signal is absent.

7. The portable electrical generator of claim 1, further comprising a remote starter in communication with the engine deactivator, a remote restart command being generated in response to an input received on the remote starter, the remote restart command being conditionally operative to restart the engine.

8. A method for deactivating an engine of a portable electrical generator comprising the steps of:
receiving from a carbon monoxide gas sensor an output electrical current proportional to a detected concentration of ambient carbon monoxide;
deriving an ambient carbon monoxide concentration value from the received output electrical current;
evaluating, on a controller, within a first control loop while the ambient carbon monoxide concentration value is below a lower threshold, a voltage value from a power supply circuit to the controller corresponding to electrical continuity therewith and an active status corresponding to a regular ongoing reception of the output electrical current;

initiating, on the controller, a pre-shutoff loop in response to the ambient carbon monoxide concentration being above an upper threshold, the pre-shutoff loop including evaluating a plurality of carbon monoxide concentration values over a predetermined duration; and generating an engine deactivation signal from the controller in response to the plurality of carbon monoxide concentration values of the predetermined duration meeting an acceptance criterion.

9. The method of claim 8, wherein the engine deactivation signal restricts an ignition electrical signal to an ignition coil driving the engine.

10. The method of claim 9, wherein electrical power to the controller is generated by the generator solely during active operation thereof, the electrical power charging a power supply capacitor connected to the power supply and to the controller.

11. The method of claim 8, further comprising:

generating an engine deactivation indicator output on a remote visual indication device in response to the plurality of carbon monoxide concentration values of the predetermined duration meeting the acceptance criterion.

\* \* \* \* \*